(12) United States Patent
Matsuo et al.

(10) Patent No.: US 8,785,660 B2
(45) Date of Patent: Jul. 22, 2014

(54) POLYOXYALKYLENE-MODIFIED LIPID AND METHOD FOR PRODUCING THE SAME

(75) Inventors: Satoshi Matsuo, Kawasaki (JP); Yuji Yamamoto, Kawasaki (JP); Chika Itoh, Kawasaki (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 13/431,590

(22) Filed: Mar. 27, 2012

(65) Prior Publication Data

US 2012/0253053 A1 Oct. 4, 2012

(30) Foreign Application Priority Data

Mar. 29, 2011 (JP) .................................. 2011-073373

(51) Int. Cl.
*C07D 207/456* (2006.01)
(52) U.S. Cl.
CPC .................................. *C07D 207/456* (2013.01)
USPC ........................................................ 548/546
(58) Field of Classification Search
CPC .................................................. C07D 207/456
USPC ........................................................ 548/546
See application file for complete search history.

(56) References Cited

U.S. PATENT DOCUMENTS

| | | | |
|---|---|---|---|
| 2003/0031704 A1* | 2/2003 | Huang et al. .................. | 424/450 |
| 2010/0076209 A1* | 3/2010 | Wu et al. ........................ | 554/79 |
| 2010/0240883 A1* | 9/2010 | Wu et al. ...................... | 536/28.51 |

OTHER PUBLICATIONS

Greene et al. (Greene, T. W.; Wuts, P. G. M. Protective Groups in Organic Synthesis, 3rd ed.; John Wiley & Sons: New York, 1991). Ch. 7 provided.*
Asako et al. (Machine translation of: JP 2010-235450 (published Oct. 21, 2010).*

* cited by examiner

*Primary Examiner* — Robert Havlin
(74) *Attorney, Agent, or Firm* — Rankin, Hill & Clark LLP (57) ABSTRACT

Provided are a thiol-reactive polyoxyalkylene-modified lipid which can be used to chemically modify bioactive substances and which can be used for drug delivery systems such as liposomes and a method for producing the same. The polyoxyalkylene-modified lipid is represented by the following formula (1):

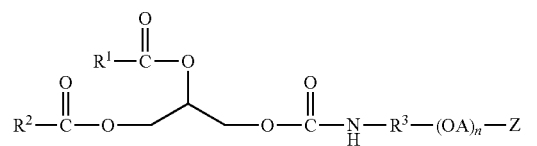

(1)

(wherein, $R^1$ and $R^2$ are hydrocarbon groups which are the same as or different from each other and which contain 4 to 24 carbon atoms, $R^3$ is a divalent hydrocarbon group containing 1 to 6 carbon atoms, OA is oxyalkylene groups containing 2 to 4 carbon atoms, n is the average addition mole number of the oxyalkylene groups and is 5 to 1,000, and Z is a group containing either maleimide or iodoacetamide.)

3 Claims, 3 Drawing Sheets

FIG. 3

POLYOXYALKYLENE-MODIFIED LIPID AND METHOD FOR PRODUCING THE SAME

TECHNICAL FIELD

The present invention relates to a thiol-reactive polyoxyalkylene-modified lipid which can be used to chemically modify bioactive substances and which can be used for drug delivery systems such as liposomes and also relates to a method for producing the same.

BACKGROUND ART

In the field of drug delivery systems, liposome formulations containing drugs such as anticancer drugs have been widely studied in the past. In such studies, various approaches to modify liposome surfaces with water-soluble polymers have been made for the purpose of increasing the retention of the liposome formulations in blood. Since a surface modified with a water-soluble polymer, for example, polyethylene glycol, has a hydration layer formed therearound, a liposome formulation thereof is unlikely to be incorporated into reticuloendothelial system (RES) tissues in blood and therefore is increased in retention in blood. In general, blood vessels around cancer tissues remain in a state of high permeability. Therefore, the longer the residence time of particles like liposomes in blood is, the more the opportunities to be incorporated into the cancer tissues are, which allows the integration efficiency of formulations to be increased.

A polyethylene glycol-modified lipid (PEG lipid) bound to a hydrophobic compound is widely used as a polyethylene glycol derivative used to modify liposomes. A polyethylene glycol-modified phospholipid (PEG phospholipid) such as diacyl phosphatidylethanolamine is cited as an example thereof. However, in recent years, the following disadvantages have been pointed out: a disadvantage that the amount of a phospholipid incorporated into cells cannot be earned because the charge of the phospholipid repels the membranes of the cells, a disadvantage that a drug cannot be efficiently contained in a liposome depending on the charge of the drug, and the like. Therefore, a diacyl glycerol-type PEG lipid having no charge is believed to be a more useful material depending on liposome formulations.

On the other hand, attempts to actively increase the delivery efficiency of formulations are being made in such a way that molecules, such as antibodies, peptides, sugar chains, and ligands, recognizing target sites are grafted to PEG terminuses. In order to graft such molecules to the PEG terminuses, the PEG terminuses need to be converted into reactive active groups in advance. For the active groups, the following groups are selected: functional groups suitable for reactions with reactive sites (for example, an amino group of a lysine side chain and a thiol group of a cysteine side chain) of antibodies, peptides, sugar chains, ligands, and the like. When PEG is bonded to an amino group of a lysine side chain or the like, an undesirable situation such as the deactivation of an active site arises in some cases. In general, cysteine is less in amount than lysine among amino acids contained in biologically relevant molecules such as proteins; hence, there is an advantage that the bonding of PEG to thiol groups is unlikely to cause the deactivation of active sites. Against such a background, for phospholipids conventionally widely used, thiol-reactive PEG phospholipids have been developed; however, only a small number of diacyl glycerol-type thiol-reactive PEG lipids have been developed.

While any example of a thiol-reactive PEG lipid is not disclosed, Patent Literature 1 describes a diacyl glycerol-type activated PEG lipid and is cited as one synthesis example applicable to the synthesis of a thiol-reactive PEG lipid. In a production method described therein, a PEG lipid protected with a benzyl ether group is deprotected under reducing conditions to produce a hydroxyl group and the hydroxyl group is converted into p-nitrophenyl carbonate, whereby an activated PEG lipid is obtained. However, since the PEG lipid is exposed to such reducing conditions, an ester group that is a linking group of the lipid is likely to be decomposed and the co-production of a monoacyl lipid is likely to be caused. Since relatively severe conditions such as oxidative conditions, acidic conditions, and alkaline conditions are required for the deprotection of a common protective group other than the exemplified benzyl ether group, the co-production of the monoacyl lipid cannot be avoided.

Furthermore, Patent Literature 2 is cited as a production method excluding deprotection. In the described production method, after the reaction of amino groups of D-glucamine with activated polyethylene glycol chains having maleimide groups, lipid chains are grafted to hydroxyl groups of D-glucamine. However, in this method, the lipid chains are not grafted to all the hydroxyl groups of D-glucamine because of steric hindrance and the like and therefore the co-production of a monoacyl lipid is caused. This problem is not mentioned therein.

Co-produced monoacyl lipids are generally referred to as lysolipids. It has been reported that the lysolipids destabilize liposomes, have strong biotoxicity, and exhibit bioactivity. These problems are highly valued in the case of using lipids as drug delivery systems and therefore a high-purity thiol-reactive polyoxyalkylene-modified lipid having a small lysolipid content is desired.

CITATION LIST

Patent Literature

[Patent Literature 1] EP 1198490
[Patent Literature 2] JP 2010235450

SUMMARY OF INVENTION

Technical Problem

It is an object of the present invention to provide a high-purity thiol-reactive polyoxyalkylene-modified lipid having a small monoacyl lipid content and a method for producing the same.

Solution to Problem

The inventors have made intensive investigations to solve the above problems. As a result, the inventors have found a high-purity thiol-reactive polyoxyalkylene-modified lipid having a small monoacyl lipid content and a method for producing the same to complete the present invention.

The present invention is characterized in that a deprotecting step in which a monoacyl lipid unsuitable for applications to drug delivery systems is co-produced is performed prior to a reaction step of coupling a polyoxyalkylene chain to lipids. In the case where a thiol-reactive polyoxyalkylene-modified lipid having a specific structure is produced in such a manner that a protective group for an amino group bonded to the polyoxyalkylene chain, an active group of a lipid derivative, and an acid used for deprotection are appropriately selected in the step, the following fact has been found: the fact that a high-purity thiol-reactive polyoxyalkylene-modified lipid having a small monoacyl lipid content is obtained without significantly reducing the purity of the active group thereof.

That is, the present invention provides:
(1) a polyoxyalkylene-modified lipid represented by Formula (1) below.

[Chem. 1]

(1)

(In the formula, $R^1$ and $R^2$ are hydrocarbon groups which are the same as or different from each other and which contain 4 to 24 carbon atoms, $R^3$ is a divalent hydrocarbon group containing 1 to 6 carbon atoms, OA is oxyalkylene groups containing 2 to 4 carbon atoms, n is the average addition mole number of the oxyalkylene groups and is 5 to 1,000, and Z is a group containing either maleimide or iodoacetamide.)

(2) A method for producing a polyoxyalkylene-modified lipid represented by Formula (1) below, characterized in that a reaction of Step (II) is performed after a reaction of Step (I) is performed.

[Chem. 2]

(1)

(In the formula, $R^1$ and $R^2$ are hydrocarbon groups which are the same as or different from each other and which contain 4 to 24 carbon atoms, $R^3$ is a divalent hydrocarbon group containing 1 to 6 carbon atoms, OA is oxyalkylene groups containing 2 to 4 carbon atoms, n is the average addition mole number of the oxyalkylene groups and is 5 to 1,000, and Z is a group containing either maleimide or iodoacetamide.)

Step (I): a step of obtaining a compound represented by Formula (3) below by deprotecting P of a compound represented by Formula (2) below with a sulfonic acid.

[Chem. 3]

$$P-R^3-(OA)_n-Z \quad (2)$$

(In the formula, OA is oxyalkylene groups containing 2 to 4 carbon atoms, n is the average addition mole number of the oxyalkylene groups and is 5 to 1,000, $R^3$ is a divalent hydrocarbon group containing 1 to 6 carbon atoms, Z is a group containing either maleimide or iodoacetamide, and P is a chemically protected amino group which is to be deprotected with acid.)

[Chem. 4]

$$X-R^3-(OA)_n-Z \quad (3)$$

(In the formula, OA is oxyalkylene groups containing 2 to 4 carbon atoms, n is the average addition mole number of the oxyalkylene groups and is 5 to 1,000, $R^3$ is a divalent hydrocarbon group containing 1 to 6 carbon atoms, Z is a group containing either maleimide or iodoacetamide, and X is an ion pair of an amino group and a sulfonic acid.)

Step (II): a step of obtaining the compound represented by Formula (1) in such a manner that a solution containing the compound represented by Formula (3) is added dropwise to a solution containing a compound represented by Formula (4) to cause reaction.

[Chem. 5]

(4)

(In the formula, $R^1$ and $R^2$ are hydrocarbon groups which are the same as or different from each other and which contain 4 to 24 carbon atoms and Y is an activated carbonate group.)

(3) In the polyoxyalkylene-modified lipid-producing method specified in (2), Z is a group containing maleimide.

(4) In the polyoxyalkylene-modified lipid-producing method specified in (2), the chemically protected amino group P which is to be deprotected with acid is a t-butyl carbamate group.

(5) In the polyoxyalkylene-modified lipid-producing method specified in (2), the sulfonic acid used to deprotect the chemically protected amino group P which is to be deprotected with acid is methanesulfonic acid.

Advantageous Effects of Invention

A thiol-reactive polyoxyalkylene-modified lipid produced according to the present invention has a small monoacyl lipid content and therefore can be one of functional materials useful in the field of drug delivery systems because biotoxicity and the self-degradation of liposomes due to contamination with a monoacyl lipid can be suppressed in the case of using the thiol-reactive polyoxyalkylene-modified lipid for raw materials for liposome formulations.

DESCRIPTION OF EMBODIMENTS

The present invention is characterized in that a deprotecting step in which a monoacyl lipid is co-produced is performed prior to a reaction step of coupling a polyoxyalkylene derivative to a lipid derivative. Upon the production thereof, in order to obtain a thiol-reactive polyoxyalkylene-modified lipid having a small monoacyl lipid content without significantly reducing the purity of an active group Z, a protective group for an amino group bonded to the polyoxyalkylene derivative, an active group of the lipid derivative, and an acid used for deprotection need to be appropriately selected.

A linking group, for example, a urethane bond, capable of readily forming a bond under mild conditions among chemical bonds needs to be selected for a group linking the polyoxyalkylene derivative to the lipid derivative for the purpose of suppressing the co-production of the monoacyl lipid. In the case of using the urethane bond for linking, an amino group needs to be grafted to either one of the lipid derivative and the polyoxyalkylene derivative. In the case of aminating tertiary carbon in the lipid derivative, the monoacyl lipid may possibly be co-produced during reaction or storage because of the basicity of an amino group. Therefore, it is desirable that a terminus of the polyoxyalkylene derivative is converted into an amino group and, on the other hand, a hydroxyl group of the lipid derivative is activated into a group, for example, an activated carbonate group. A bond formed by the polyoxyalkylene derivative and the lipid derivative is a urethane bond in a compound, represented by Formula (1), having oxycarbonyl (—O—(C=O)—) on the lipid compound side and a nitrogen atom (—NH—) on the polyoxyalkylene side. Since a side reaction may possibly occur when a terminus of the polyoxyalkylene derivative is converted into an active group Z, the amino group thereof needs to be protected in advance. The polyoxyalkylene derivative having the protected amino group and the active group Z is a compound represented by Formula (2). After deprotection, the reactivity of the amino group needs to be suppressed by forming an ion pair with acid such that no side reaction occurs between the amino group and the active group Z. For this reason, a protective group capable of being deprotected with acid needs to be selected for the protection of the amino group. The active group Z is decomposed depending on the type of an acid used for deprotection and therefore may possibly be reduced in purity. The reduction in purity of the active group Z causes a problem that the delivery efficiency of a formulation cannot be increased as expected in some cases because molecules recognizing an affected area cannot be introduced as designed in the case of using a drug delivery system. Thus, in the present invention, it is necessary that the active group Z in the compound represented by Formula (1) is maleimide or iodoacetamide, which is known as a thiol-reactive group, and an appropriate acid, for example, a sulfonic acid such as methanesulfonic acid, not significantly reducing the purity of Z is selected.

As described above, the present invention contrives a production method in which the protective group for the amino group bonded to the polyoxyalkylene derivative and the active group of the lipid compound are appropriately selected and a reaction step of coupling a compound represented by Formula (3) to a compound represented by Formula (4) is performed subsequently to a step of deprotecting the compound represented by Formula (2), thereby enabling the production of a high-purity thiol-reactive polyoxyalkylene-modified lipid having a small monoacyl lipid content.

The implementation of the present invention is described below.

[Chem. 6]

In a thiol-reactive polyoxyalkylene-modified lipid, represented by Formula (1), according to the present invention, $R^1$ and $R^2$ are hydrocarbon groups which are the same as or different from each other and which contain 4 to 24 carbon atoms. The "hydrocarbon groups containing 4 to 24 carbon atoms" are, for example, linear or branched alkyl groups containing 4 to 24 carbon atoms, linear or branched alkenyl groups containing 4 to 24 carbon atoms and 1 to 3 double bonds, or the like and are preferably linear or branched alkyl groups containing 11 to 23 carbon atoms or linear or branched alkenyl groups containing 11 to 23 carbon atoms and 1 to 3 double bonds.

In a preferred embodiment of the present invention, $R^1CO$ and $R^2CO$ each represent an acyl group, derived from an aliphatic acid, containing 5 to 25 carbon atoms (preferably 12 to 24 carbon atoms). The following groups can be cited as examples of $R^1CO$ and $R^2CO$: for example, acyl groups derived from saturated and unsaturated, linear or branched aliphatic acids such as butyric acid, isobutyric acid, caproic acid, caprylic acid, capric acid, lauric acid, myristic acid, palmitic acid, palmitoleic acid, stearic acid, isostearic acid, oleic acid, linoleic acid, arachidic acid, behenic acid, erucic acid, and lignoceric acid. $R^1CO$ and $R^2CO$ may be the same as or different from each other. When the number of carbon atoms in each of $R^1$ and $R^2$ exceeds 24, a problem arises in forming a liposome because dispersion in an aqueous phase is poor. When the number of carbon atoms in each of $R^1$ and $R^2$ is less than 4, a problem arises in forming a liposome because hydrophobicity is low and an interaction with the membrane of the liposome is weak.

In Formula (1), oxyalkylene groups represented by OA are oxyalkylene groups containing 2 to 4 carbon atoms and preferably 2 or 3 carbon atoms. For example, oxyethylene groups, oxypropylene groups, oxytrimethylene groups, oxybutylene groups, and the like are cited. In general, oxyalkylene groups containing a smaller number of carbon atoms have higher hydrophilicity; hence, the oxyethylene groups and the oxypropylene groups are preferred and the oxyethylene groups are more preferred. The oxyalkylene groups in a number represented by n are present in each molecule. The oxyalkylene groups may be a single type and two or more types may be combined. The combination thereof is not particularly limited. The oxyalkylene groups may be blockish or random.

In Formula (1), n represents the average addition mole number of the oxyalkylene groups (OA) and is a number of 5 to 1,000, preferably 10 to 500. When n is less than 5, the effect of retention in blood obtained by a polyoxyalkylene chain is small. When n is greater than 1,000, the polyoxyalkylene derivative represented by Formula (3) and the lipid derivative represented by Formula (4) have reduced reactivity and the compound represented by Formula (1) has increased viscosity to cause a reduction in workability, which is not preferred.

In Formula (1), $R^3$ is a portion of a linker linking the polyoxyalkylene derivative to the lipid derivative and is a divalent hydrocarbon group containing 1 to 6 carbon atoms. When the number of carbon atoms in $R^3$ is greater than 6, crystallinity is poor and purification is difficult. The following groups are cited as the hydrocarbon group: for example, a linear or branched alkylene group containing 1 to 6 carbon atoms, a linear or branched alkenylene group containing 2 to 6 carbon atoms, a linear or branched alkynylene group containing 2 to 6 carbon atoms, and the like. In particular, a methylene group, an ethylene group, a trimethylene group, a tetramethylene group, a vinylene group, a propylene group, and the like are cited. The ethylene group and the trimethylene group are preferred.

In Formula (1), Z is a group containing either maleimide or iodoacetamide and is preferably a group containing maleimide. In particular, Z has a linker linking maleimide or iodoacetamide to the polyoxyalkylene derivative and is represented by Formula (5) below.

[Chem. 7]

(5)

(In the formula, j and k are independently an integer of 0 to 6 and L represents an amide bond, a urethane bond, an ester bond, an ether bond, or a single bond.)

The thiol-reactive polyoxyalkylene-modified lipid, represented by Formula (1), according to the present invention is obtained by a production method characterized in that a reaction of Step (II) is performed after a reaction of Step (I) is performed.

Each step is described below in detail.

Step (I) is a step of obtaining the compound represented by Formula (3) by deprotecting a protective group for a chemically protected amino group P of the compound represented by Formula (2) using acid, the chemically protected amino group P being to be deprotected with acid.

The chemically protected amino group P, which is to be deprotected acid, is not particularly limited and is a protected amino group capable of being deprotected with acid. For example, the following group may be used: a known protected amino group described in PROTECTIVE GROUPS IN ORGANIC SYTHESIS (authors: Peter G. M. WUTS and THEODORA W. GREENE, publisher: John Wiley & Sons, Inc.) or the like. In particular, the following groups are cited as the chemically protected amino group P, which is to be deprotected with acid: a methyl carbamate group, an ethyl carbamate group, a tert-butyl carbamate group, a trimethylsilylethyl carbamate group, an adamantyl carbamate group, an acetamide group, a trifluoroacetamide group, a benzamide group, and the like. The tert-butyl carbamate group is preferred.

In general, an amino group forms a structure represented by Formula (6) below in the presence of acid.

[Chem. 8]

(6)

In the formula, $A^-$ is a conjugate base of an acid HA that has a monovalent negative charge. $A^-$ and $-NH_3^+$ form a zwitterion represented by Formula (6). An ion pair of an amino group and an acid refers to the zwitterion. An ion pair of an amino group represented by X in Formula (3) and a sulfonic acid refers to a similar zwitterion. A sulfonic acid used for deprotection is particularly methanesulfonic acid, benzenesulfonic acid, p-toluenesulfonic acid, or the like and is preferably methanesulfonic acid. Methanesulfonic acid has slightly lower acidity as compared to benzenesulfonic acid and p-toluenesulfonic acid and therefore slightly degrades a polyoxyalkylene chain. After deprotection, for example, methanesulfonic acid forms an ion pair represented by Formula (6-1) below together with an amino group.

[Chem. 9]

(6-1)

For example, acids such as hydrochloric acid and trifluoroacetic acid are cited as other acids introduced in PROTECTIVE GROUPS IN ORGANIC SYNTHESIS (authors: Peter G. M. WUTS and THEODORA W. GREENE, publisher: John Wiley & Sons, Inc.) or the like. In the case of using these acids, there is a problem in that amino groups and Z cause side reactions and high-molecular weight impurities are caused by the reaction of the polyoxyalkylene derivative, though it is predicted that ion pairs of the amino groups and these acids are not sufficiently formed. Furthermore, high-molecular weight impurities are caused during cryopreservation and therefore expansion into commercial production is difficult.

The reaction temperature of deprotection is not particularly limited and is preferably 10° C. to 70° C. and more preferably 15° C. to 55° C.

The mole number of the sulfonic acid, which is used for deprotection, is preferably 1 to 100 times the mole number of the polyoxyalkylene derivative, more preferably 2 to 40 times, and further more preferably 4 to 20 times. When the mole number of the sulfonic acid greater than 100 times, it is difficult to remove an excess of the sulfonic acid and therefore operation handling is poor. When the mole number thereof is less than 1 time, the amount of the sulfonic acid is insufficient to form an ion pair together with the amino group and therefore high-molecular weight impurities may possibly be caused.

Step (II) is a step of obtaining the compound represented by Formula (1) by the reaction of the compound represented by Formula (3) with the compound represented by Formula (4). Y of Formula (4) is not particularly limited and is an activated carbonate group reactive with an amino group. Y thereof is preferably a p-nitrophenyl carbonate group or a succinimidyl carbonate group. From the viewpoint of reactivity, the succinimidyl carbonate group is more preferred.

The temperature of the reaction of the compound represented by Formula (3) with the compound represented by Formula (4) is not particularly limited and is preferably 10° C. to 70° C. and more preferably 15° C. to 55° C. When the reaction temperature is lower than 10° C., the reaction of the polyoxyalkylene derivative with the lipid derivative may possibly not proceed. When the reaction temperature is higher than 70° C., a monoacyl lipid may possibly be co-produced by thermal history.

A method for mixing the compound represented by Formula (3) with the compound represented by Formula (4) is in such a way that a solution containing the compound represented by Formula (3) is added dropwise to a solution containing the compound represented by Formula (4). In this operation, the solution containing the compound represented by Formula (4) preferably contains an organic base below. The organic base is not particularly limited and is a tertiary amine capable of dissociating an ion pair of the amino group and the sulfonic acid. The organic base is preferably triethylamine, pyridine, or N,N-dimethyl-4-aminopyridine and more preferably triethylamine. The mole number of the organic base used for reaction is preferably 1 to 20 times the mole number of the polyoxyalkylene derivative, more preferably 2 to 10 times, and further more preferably 3 to 5 times. When the mole number of the organic base is greater than 20 times, it is difficult to remove an excess of the organic base and therefore operation handling is poor. When the mole number thereof is less than 1 time, there is a problem in that the polyoxyalkylene derivative remains unreacted because the amount of the organic base is insufficient to dissociate the ion pair of the amino group and the sulfonic acid.

In the case of adding the compound represented by Formula (3) in one shot, a large amount of a polyoxyalkylene amine separated from the ion pair of the sulfonic acid remains in a reaction system; hence, the amino group and Z cause side reactions and high-molecular weight impurities are likely to be caused by the reaction of the polyoxyalkylene derivative.

A method for producing the thiol-reactive polyoxyalkylene-modified lipid, which is the compound represented by Formula (1), is described below with reference to particular functional groups. This step is not limited to this.

Step (I): a step of deprotecting a polyethylene glycol maleimide compound
(In Formulae (2) and (3), P represents a chemically protected amino group (tert-butyl carbamate group) which is to be deprotected with acid, X represents an ion pair of an amino group and methanesulfonic acid, Z represents a group containing maleimide, and OA represents oxyalkylene groups.)

A compound which is represented by Formula (2) and in which a terminus of a polyethylene glycol chain is a maleimide group and another terminus thereof is the chemically protected amino group (tert-butyl carbamate group) is dissolved in a reaction solvent such as dichloromethane. The reaction solvent is not particularly limited and is preferably an organic solvent dissolving polyethylene glycol and methanesulfonic acid. Next, methanesulfonic acid is added to a solution containing the compound represented by Formula (2), followed by a deprotection reaction at 25° C. It is important that the mole number of methanesulfonic acid added thereto is greater than or equal to at least the mole number of the polyoxyalkylene derivative and an ion pair of methanesulfonic acid and an amino group is formed. In this step, a compound (3) in which a terminus of the polyoxyalkylene derivative is a maleimide group and another terminus thereof is the ion pair of the amino group and methanesulfonic acid is obtained.

Step (II): a reaction step of coupling the polyethylene glycol maleimide compound to the lipid derivative
(In Formula (4), Y represents a succinimidyl carbonate group and $R^1CO$ and $R^2CO$ each represent an acyl group derived from stearic acid.)

The lipid derivative, which is represented by Formula (4) and to which the succinimidyl carbonate group is introduced, is dissolved in a reaction solvent such as toluene. The reaction solvent is not particularly limited and is preferably an organic solvent dissolving the lipid derivative, polyethylene glycol, and the organic base. Next, the organic base, which is triethylamine, is added to a solution containing the lipid derivative. The type of the organic base added thereto is not particularly limited and is one capable of dissociating the ion pair of methanesulfonic acid and the amino group. It is important that the mole number of the organic base added thereto is greater than or equal to at least the mole number of methanesulfonic acid forming an ion pair and the organic base in an amount sufficient to dissociate the ion pair of methanesulfonic acid and the amino group is added. Next, the compound which is represented by Formula (3) and which is obtained in Step (I) is dissolved in toluene. The toluene solution is added dropwise to a mixed solution of the lipid derivative and the organic base, followed by reaction at 25° C.

In the case of adding the toluene solution, which contains the compound represented by Formula (3), in one shot, a large amount of a polyoxyalkylene amine compound separated from the ion pair of methanesulfonic acid remains in a reaction system; hence, the amino group and Z cause side reactions and high-molecular weight impurities are likely to be caused by the reaction of the polyoxyalkylene derivative. Therefore, it is important to add the toluene solution, which contains the compound represented by Formula (3), dropwise. In this step, polyoxyalkylene-modified lipid having a maleimide group, that is, the compound represented by Formula (1) is obtained.

In the production method, the protective group for the amino group bonded to the polyoxyalkylene derivative, the active group of the lipid compound, and acid used for deprotection are appropriately selected and the reaction step of coupling the polyoxyalkylene derivative to the lipid derivative is performed subsequently to the step of deprotecting the polyoxyalkylene derivative. The production method enables the production of a high-purity thiol-reactive polyoxyalkylene-modified lipid having a small monoacyl lipid content. A thiol-reactive polyoxyalkylene-modified lipid produced according to the present invention can be one of functional materials useful in the field of drug delivery systems because biotoxicity and the self-degradation of liposomes due to contamination with a monoacyl lipid can be suppressed.

EXAMPLES

The present invention is further described below in detail on the basis of examples. NMR, GPC, and TLC were used to analyze or identify compounds in the examples.

<$^1$H-NMR Analysis Method>
In $^1$H-NMR analysis, JNM-ECP 400 and JNM-ECA 600 manufactured by JEOL Datum Ltd. were used. The integrals of NMR measurements are theoretical values.

<GPC Analysis Method>
A GPC system used was LC 10AVP and measurement was performed under conditions below.
Developing solvent: DMF
Flow rate: 0.7 ml/min
Columns: PLgel MIXED-D, two
Column temperature: 40° C.
Detector: RI (manufactured by shodex)
Amount of sample: 1 mg/mL, 100 μL
GPC measurements were described together with analytical values for main peaks obtained by cutting off high-molecular weight impurities and low-molecular weight impurities from elution curves perpendicularly from points of inflection to the baselines of the elution curves and analytical values for whole peaks from the start point to end point of elution.

<TLC Analysis>
Silica gel plates produced by Merck were used for thin-layer chromatography. After development was performed with a solvent mixture of chloroform/methanol=85/15 (v/v) and color development was performed with iodine, sample spots were obtained.

Example 1

Example 1-1: a step of maleimidizing a polyethylene glycol compound

Example 1-2: a step of deprotecting a polyethylene glycol maleimide compound

Example 1-3: a reaction step of coupling a polyethylene glycol maleimide compound to a lipid compound The synthesis of a compound, represented by Formula (1), obtained through the steps of Examples 1-1, 1-2, 1-3 in that order

[Chem. 10]

(A)

n = about 45

($R^1CO$ and $R^2CO$=acyl groups derived from stearic acid, $R^3$=a trimethylene group, OA=oxyethylene groups, n=45, Z=$(CH_2)_j$-L-$(CH_2)_k$—W; j=0, L=an amide bond, k=2, W=a maleimide group)

Example 1-1

A Step of Maleimidizing a Polyethylene Glycol Compound

Into a 100-mL round-bottomed flask equipped with a thermometer, a nitrogen-blowing tube, an agitator, and a cooling tube, 34 g of acetonitrile, 6.8 g (3.4 mmol) of a polyethylene glycol ethylamine compound protected with t-butyl carbamate, and 1.1 g (4.1 mmol) of succinimidyl maleimide propionate were put, followed by agitation with nitrogen blown into the flask and reaction at 25° C. for 2 hours. After reaction was terminated, a reaction solution was transferred to a 200-mL eggplant flask, acetonitrile was distilled off at 50° C. using an evaporator, and a remaining concentrate was dissolved in 48 g of ethyl acetate. Thereafter, the ethyl acetate solution was cooled to 10° C. and 27 g of hexane was added to the ethyl acetate solution, followed by crystallization. Precipitated crystals were vacuum-filtered. After 48 g of ethyl acetate was added to obtained crystals and the crystals were heated and were dissolved therein at 40° C., this ethyl acetate solution was cooled to 10° C. and 27 g of hexane was added to this ethyl acetate solution, followed by crystallization. Thereafter, after similar crystallization was repeated three times, followed by washing with hexane, crystals were obtained by filtration and were then dried, whereby a polyethylene glycol maleimide compound (A) protected with t-butyl carbamate was obtained as described below.

Characteristic peaks observed by $^1$H-NMR (CDCl$_3$, internal standard TMS) were as described below.

δ (ppm): 1.44 (12H, s, (CH$_3$)$_3$C—OC(=O)NH—CH$_2$—CH$_2$—) 1.75 (2H, t, (CH$_3$)$_3$C—OC(=O)NH—CH$_2$—CH$_2$—) 2.50-2.53 (2H, t, —CH$_2$—CH$_2$—NH—C(=O)NH—CH$_2$—CH$_2$-Maleimide) 3.21-3.24 (2H, m, (CH$_3$)$_3$C—OC(=O)NH—CH$_2$—CH$_2$—) 3.40-3.80 (182H, m, —CH$_2$(OCH$_2$CH$_2$)$_m$OCH$_2$—CH$_2$—), (2H, t, —CH$_2$(OCH$_2$CH$_2$)$_m$OCH$_2$—CH$_2$—), (2H, t, —CH$_2$(OCH$_2$CH$_2$)$_m$OCH$_2$—CH$_2$—), (2H, t, —CH$_2$(OCH$_2$CH$_2$)$_m$OCH$_2$—CH$_2$—) 5.00 (1H, s, (CH$_3$)$_3$C—OC(=O)NH—CH$_2$—CH$_2$—) 6.27 (1H, s, —CH$_2$—CH$_2$—NH—C(=O)—CH$_2$—CH$_2$-Maleimide) 6.70 (1H, s, —CH$_2$—CH$_2$—NH—C(=O)—CH$_2$—CH$_2$-Maleimide)

GPC Analysis; number-average molecular weight (Mn): 2,293, weight-average molecular weight (Mw): 2,355, polydispersity (Mw/Mn): 1.049, peak top molecular weight (Mp): 2,304

Example 1-2

A Step of Deprotecting a Polyethylene Glycol Maleimide Compound

Into a 100-mL round-bottomed flask equipped with a thermometer, a nitrogen-blowing tube, an agitator, and a cooling tube, 45 g of dichloromethane, 5.7 g (2.5 mmol) of the polyethylene glycol maleimide compound (A) protected with t-butyl carbamate, and 2.4 g (25 mmol) of methanesulfonic acid were put, followed by agitation with nitrogen blown into the flask and reaction at 25° C. for 3 hours. After reaction was terminated, a reaction solution was transferred to a 200-mL eggplant flask, dichloromethane was distilled off at 50° C. using an evaporator, and a remaining concentrate was dissolved in 50 g of ethyl acetate. After 2.9 g of an acid adsorbent, KW1000, was added to the solution and the solution was agitated at room temperature for 1 hour, impurities and the adsorbent were removed by filtration. Thereafter, the filtrate was cooled to 10° C. and 50 g of hexane was added to the filtrate, followed by crystallization. Precipitated crystals were vacuum-filtered. After the obtained crystals were washed with hexane, the crystals were obtained by filtration and were then dried, whereby a polyethylene glycol maleimide compound (B) forming a methanesulfonate salt was obtained as described below.

Characteristic peaks observed by $^1$H-NMR (CDCl$_3$, internal standard TMS) were as described below.

δ (ppm): 1.95-2.15 (2H, m, CH$_3$S(=O)$_2$O$^-$.NH$_3^+$—CH$_2$—CH$_2$—) 2.50-2.53 (2H, t, —CH$_2$—CH$_2$—NH—C(=O)—CH$_2$—CH$_2$-Maleimide) 2.77 (2H, m, CH$_3$S(=O)$_2$O$^-$.NH$_3^+$—CH$_2$—CH$_2$—) 3.21-3.24 (2H, m, CH$_3$S(=O)$_2$O$^-$.NH$_3^+$—CH$_2$—CH$_2$—) 3.40-3.80 (182H, m, —CH$_2$(OCH$_2$CH$_2$)$_m$OCH$_2$—CH$_2$—), (2H, t, —CH$_2$(OCH$_2$CH$_2$)$_m$OCH$_2$—CH$_2$—), (2H, t, —CH$_2$(OCH$_2$CH$_2$)$_m$OCH$_2$—CH$_2$—), (2H, t, —CH$_2$(OCH$_2$CH$_2$)$_m$OCH$_2$—CH$_2$—) 6.27 (1H, s, —CH$_2$—CH$_2$—

NH—C(=O)—CH$_2$—CH$_2$-Maleimide) 6.70 (1H, s, —CH$_2$—CH$_2$—NH—C(=O)—CH$_2$—CH$_2$-<u>Maleimide</u>)

GPC Analysis; number-average molecular weight (Mn): 2,061, weight-average molecular weight (Mw): 2,141, polydispersity (Mw/Mn): 1.067, peak top molecular weight (Mp): 2,124

[Chem. 11]

(B)

n = about 45

Figure 2:
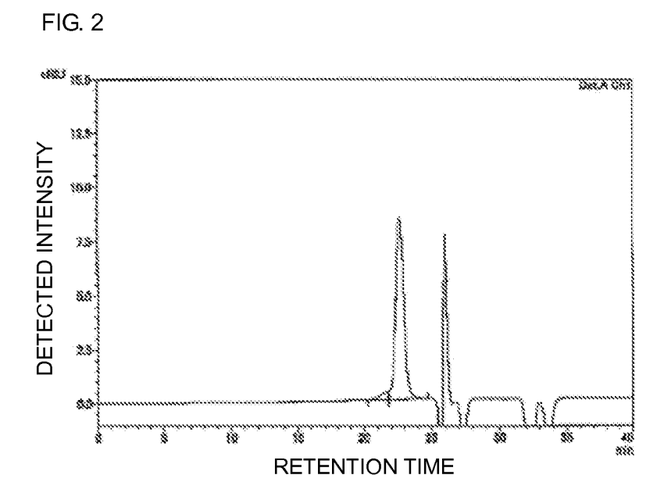
FIG. 2 shows GPC analysis results of a compound (B) obtained in Example 1.

Results obtained by analyzing the obtained compound (B) were shown in FIG. 2.

Example 1-3

A Reaction Step of Coupling a Polyethylene Glycol Maleimide Compound To a Lipid Compound Into a 100-mL round-bottomed flask equipped with a thermometer, a nitrogen-blowing tube, an agitator, and a cooling tube, 17 g of toluene, 2.3 g (3.0 mmol) of distearoylglyceryl succinimidyl carbonate, and 0.5 g (5.0 mmol) of triethylamine were put, followed by agitation with nitrogen blown into the flask and dissolution. Into a 100-mL round-bottomed flask equipped with a thermometer, a nitrogen-blowing tube, an agitator, and a cooling tube, 34 g of toluene and 5.2 g (2.5 mmol) of the polyethylene glycol maleimide compound (B) forming the methanesulfonate salt were put, followed by agitation with nitrogen blown into the flask and dissolution. The toluene solution containing the polyethylene glycol maleimide compound was added dropwise to the toluene solution containing distearoylglyceryl succinimidyl carbonate, followed by reaction at 40° C. for 2 hours. After reaction was terminated, 1.6 g of an acid adsorbent, KW1000, and 0.3 g of an alkali adsorbent, KW700, were added to a reaction solution. After the reaction solution was agitated at room temperature for 1 hour, impurities and the adsorbents were removed by filtration. After toluene was distilled off from the filtrate at 50° C. using an evaporator, a remaining concentrate was dissolved in ethanol. Ethanol was distilled off at 50° C. using the evaporator again. The concentrate was dried, whereby a maleimidized polyethylene glycol-modified lipid (C) was obtained.

Characteristic peaks observed by $^1$H-NMR (CDCl$_3$, internal standard TMS) were as described below.

δ (ppm): 0.88 (6H, t, <u>CH$_3$</u> (CH$_2$)$_{14}$—CH$_2$—CH$_2$—CO(=O)—) 1.25 (56H, m, CH$_3$(<u>CH$_2$</u>)$_{14}$CH$_2$—CH$_2$—CO(=O)—) 2.50-2.53 (2H, t, —CH$_2$—CH$_2$—NH—C(=O)NH— <u>CH$_2$</u>—CH$_2$-Maleimide) 3.21-3.24 (2H, m, (CH$_3$)$_3$C—OC(=O)NH—<u>CH$_2$</u>—CH$_2$—) 3.40-3.80 (182H, m, —CH$_2$(O<u>CH$_2$CH$_2$</u>)$_m$OCH$_2$—CH$_2$—), (2H, t, —CH$_2$(OCH$_2$CH$_2$)$_m$O<u>CH$_2$</u>—CH$_2$—), (2H, t, —<u>CH$_2$</u>(OCH$_2$CH$_2$)$_m$OCH$_2$—<u>CH$_2$</u>—), (2H, t, —<u>CH$_2$</u>(OCH$_2$CH$_2$)$_m$OCH$_2$—CH$_2$—) 6.27 (1H, s, —CH$_2$—CH$_2$—<u>NH</u>—C(=O)—CH$_2$—CH$_2$-Maleimide) 6.70 (1H, s, —CH$_2$—CH$_2$—NH—C(=O)—CH$_2$—CH$_2$-<u>Maleimide</u>)

[Chem. 12]

(C)

n = about 45

Figure 1:
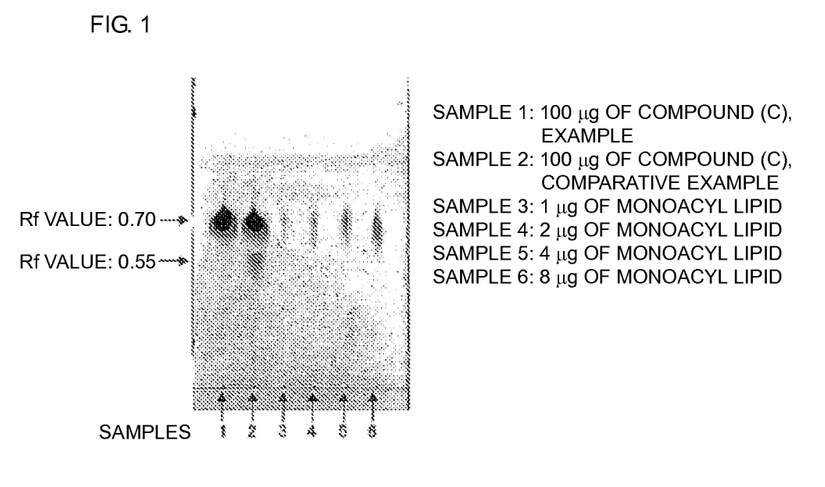
FIG. 1 shows TLC analysis results obtained by separating and developing each sample by thin-layer chromatography. After being the sample was developed with chloroform/methanol=85/15, spots were confirmed by color development with iodine. Sample 1 is 100 µg of a compound (C) obtained by a production method of Example 1, Sample 2 is 100 µg of a compound (C) obtained by a production method of Comparative Example 1, Sample 3 is 1 µg of a monoacyl lipid, Sample 4 is 2 µg of a monoacyl lipid, Sample 5 is 4 µg of a monoacyl lipid, and Sample 6 is 8 µg of a monoacyl lipid.

After being developed by TLC (thin-layer chromatography: chloroform/methanol=85/15), the obtained compound (C) was confirmed by color development with iodine (FIG. 1).

Comparative Example 1

Comparative Example 1-1: a reaction step of coupling a polyethylene glycol compound to a lipid compound Comparative Example 1-2: a step of deprotecting a polyethylene glycol-modified lipid Comparative Example 1-3: a step of maleimidizing the polyethylene glycol-modified lipid The synthesis of a compound represented by Formula (1) obtained through the steps of Examples 1-1, 1-2, 1-3 ($R^1$CO and $R^2$CO=acyl groups derived from stearic acid, $R^3$=a trimethylene group, OA=oxyethylene groups, n=45, Z=(CH$_2$)$_j$-L-(CH$_2$)$_k$—W; j=0, L=an amide bond, k=2, W=a maleimide group)

Comparative Example 1-1

A Reaction Step of Coupling a Polyethylene Glycol Compound to a Lipid Compound Into a 100-mL round-bottomed flask equipped with a thermometer, a nitrogen-blowing tube, an agitator, and a cooling tube, 34 g of toluene, 6.8 g (3.4 mmol) of a polyethylene glycol propylamine compound protected with t-butyl carbamate, and 3.1 g (4.1 mmol) of distearoylglyceryl succinimidyl carbonate were put, followed by agitation with nitrogen blown into the flask and reaction at 40° C. for 2 hours. After reaction was terminated, 2.0 g of an acid adsorbent, KW1000, and 0.3 g of an alkali adsorbent, KW700, were added to a reaction solution. After the reaction solution was agitated at room temperature for 1 hour, impurities and the adsorbents were removed by filtration. After toluene was distilled off from the filtrate at 50° C. using an evaporator, a remaining concentrate was dissolved in ethanol. Ethanol was distilled off at 50° C. using the evaporator again. The concentrate was dried, whereby a polyethylene glycol-modified lipid (D) protected with t-butyl carbamate was obtained.

Characteristic peaks observed by $^1$H-NMR (CDCl$_3$, internal standard TMS) were as described below.

δ (ppm): 0.88 (6H, t, $\underline{CH_3}(CH_2)_{14}$—CH$_2$—CH$_2$—CO(=O)—) 1.25 (56H, m, CH$_3$ $\underline{(CH_2)_{14}}$—CH$_2$—CH$_2$—CO(=O)—) 1.75 (2H, t, (CH$_3$)$_3$C—OC(=O)NH—CH$_2$—$\underline{CH_2}$—) 3.21-3.24 (2H, m, (CH$_3$)$_3$C—OC(=O)NH—$\underline{CH_2}$—CH$_2$—) 3.40-3.80 (182H, m, —CH$_2$(O$\underline{CH_2CH_2}$)$_m$OCH$_2$—CH$_2$—), (2H, t, —CH$_2$(OCH$_2$CH$_2$)$_m$O$\underline{CH_2}$—CH$_2$—), (2H, t, —CH$_2$ (OCH$_2$CH$_2$)$_m$OCH$_2$—$\underline{CH_2}$—), (2H, t, —$\underline{CH_2}$(OCH$_2$CH$_2$)$_m$OCH$_2$—CH$_2$—)

[Chem. 13]

(D)

n = about 45

Comparative Example 1-2

A Step of Deprotecting a Polyethylene Glycol-modified Lipid

Into a 100-mL round-bottomed flask equipped with a thermometer, a nitrogen-blowing tube, an agitator, and a cooling tube, 45 g of dichloromethane, 6.5 g (2.5 mmol) of the polyethylene glycol-modified lipid (D) protected with t-butyl carbamate, and 2.4 g of methanesulfonic acid were put, followed by agitation with nitrogen blown into the flask and reaction at 25° C. for 3 hours. After reaction was terminated, a reaction solution was transferred to a 200-mL eggplant flask, dichloromethane was distilled off 50° C. using an evaporator, and a remaining concentrate was dissolved in 50 g of ethyl acetate. After 2.9 g of an acid adsorbent, KW1000, was added to the solution and the solution was agitated at room temperature for 1 hour, impurities and the adsorbent were removed by filtration. After ethyl acetate was distilled off from the filtrate at 50° C. using an evaporator, a remaining concentrate was dissolved in ethanol. Ethanol was distilled off at 50° C. using the evaporator again. The concentrate was dried, whereby a polyethylene glycol-modified lipid (E) forming a methanesulfonate salt was obtained.

Characteristic peaks observed by $^1$H-NMR (CDCl$_3$, internal standard TMS) were as described below.

δ (ppm): 0.88 (6H, t, $\underline{CH_3}(CH_2)_{14}$—CH$_2$—CH$_2$—CO(=O)—) 1.25 (56H, m, CH$_3\underline{(CH_2)_{14}}$—CH$_2$—CH$_2$—CO(=O)—) 2.77 (2H, m, CH$_3$S(=O)$_2$O$^-$.NH$_3^+$—CH$_2$—CH$_2$—) 3.21-3.24 (2H, m, (CH$_3$)$_3$C—OC(=O)NH—$\underline{CH_2}$—CH$_2$—) 3.40-3.80 (182H, m, —CH$_2$(O$\underline{CH_2CH_2}$)$_m$OCH$_2$—CH$_2$—), (2H, t, —CH$_2$(OCH$_2$CH$_2$)$_m$O$\underline{CH_2}$—CH$_2$—), (2H, t, —CH$_2$ (OCH$_2$CH$_2$)$_m$OCH$_2$—$\underline{CH_2}$—), (2H, t, —$\underline{CH_2}$(OCH$_2$CH$_2$)$_m$OCH$_2$—CH$_2$—)

[Chem. 14]

(E)

n = about 45

Comparative Example 1-3

A Step of Maleimidizing the Polyethylene Glycol-modified Lipid

Into a 100-mL round-bottomed flask equipped with a thermometer, a nitrogen-blowing tube, an agitator, and a cooling tube, 34 g of acetonitrile, 5.2 g (2.0 mmol) of the polyethylene glycol-modified lipid (E), and 0.6 g (2.4 mmol) of succinimidyl maleimide propionate were put, followed by agitation with nitrogen blown into the flask and reaction at 25° C. for 2 hours. After reaction was terminated, acetonitrile was distilled off at 50° C. using an evaporator and a concentrate was dissolved in 50 g of ethyl acetate. After 0.8 g of an acid adsorbent, KW1000, was added to the solution and the solution was agitated at room temperature for 1 hour, impurities and the adsorbent were removed by filtration. After ethyl acetate was distilled off from the filtrate at 50° C. using an evaporator, a remaining concentrate was dissolved in ethanol. Ethanol was distilled off at 50° C. using the evaporator again. The concentrate was dried, whereby a maleimidized polyethylene glycol-modified lipid (C) was obtained.

Characteristic peaks observed by $^1$H-NMR (CDCl$_3$, internal standard TMS) were as described below.

δ (ppm): 0.88 (6H, t, $\underline{CH_3}(CH_2)_{14}$—$CH_2$—$CH_2$—CO(=O)—) 1.25 (56H, m, $CH_3\underline{(CH_2)_{14}}$—$CH_2$—$CH_2$—CO(=O)—) 2.50-2.53 (2H, t, —$CH_2$—$CH_2$—NH—C(=O)NH—$CH_2$—$CH_2$-Maleimide) 3.40-3.80 (182H, m, —$CH_2$(O$\underline{CH_2CH_2}$)$_m$O$CH_2$—$CH_2$—), (2H, t, —$CH_2$(O$CH_2CH_2$)$_m$O$\underline{CH_2}$—$CH_2$—), (2H, t, —$CH_2$(O$CH_2CH_2$)$_m$O$CH_2$—$\underline{CH_2}$—), (2H, t, —$\underline{CH_2}$(O$CH_2CH_2$)$_m$O$CH_2$—$CH_2$—) 6.27 (1H, s, —$CH_2$—$CH_2$—$\underline{NH}$—C(=O)—$CH_2$—$CH_2$-Maleimide) 6.70 (1H, s, —$CH_2$—$CH_2$—NH—C(=O)—$CH_2$—$CH_2$-Maleimide)

After being developed by TLC (thin-layer chromatography: chloroform/methanol=85/15), the obtained compound (C) was confirmed by color development with iodine (FIG. 1).

In Sample 2 synthesized in Comparative Example 1, the polyethylene glycol-modified lipid was exposed to deprotection conditions and therefore an ester group of a lipid residue was decomposed; hence, the co-production of 4% to 8% of a monoacyl lipid was confirmed at a position with an Rf value of 0.55 on a thin-layer chromatogram shown in FIG. 1. In contrast to Comparative Example 1, in Sample 1 synthesized in Example 1, the polyethylene glycol-modified lipid was not exposed to deprotection conditions and therefore no monoacyl lipid was co-produced. As a result, a target substance was capable of being obtained at high purity.

Comparative Example 2

The synthesis of a compound represented by Formula (F) obtained using trifluoroacetic acid during deprotection in Example 1-2

(X=an ion pair of an amino group and trifluoroacetic acid, Z=(CH$_2$)$_j$-L-(CH$_2$)$_k$—W; J=0, L=an amide bond, k=2, W=a maleimide group, R$^3$=a trimethylene group, OA=oxyethylene groups, n=45)

Into a 100-mL round-bottomed flask equipped with a thermometer, a nitrogen-blowing tube, an agitator, and a cooling tube, 45 g of dichloromethane, 5.7 g (2.5 mmol) of a polyethylene glycol maleimide compound (A) protected with t-butyl carbamate, and 2.8 g (25 mmol) of trifluoroacetic acid were put, followed by agitation with nitrogen blown into the flask and reaction at 25° C. for 3 hours. After reaction was terminated, a reaction solution was transferred to a 200-mL eggplant flask, dichloromethane was distilled off at 50° C. using an evaporator, and a remaining concentrate was dissolved in 50 g of ethyl acetate. After 2.9 g of an acid adsorbent, KW1000, was added to the solution and the solution was agitated at room temperature for 1 hour, impurities and the

[Chem. 15]

(C)

n = about 45 adsorbent were removed by filtration. Thereafter, the filtrate was cooled to 10° C. and 50 g of hexane was added to the filtrate, followed by crystallization. Precipitated crystals were vacuum-filtered. After the obtained crystals were washed with hexane, the crystals were obtained by filtration and were then dried, whereby a polyethylene glycol maleimide compound (F) forming a trifluoroacetate salt was obtained as described below.

Characteristic peaks observed by $^1$H-NMR (CDCl$_3$, internal standard TMS) were as described below.

δ (ppm): 1.95-2.15 (2H, m, CF$_3$C(=O)$_2$O$^-$.NH$_3^+$—CH$_2$—CH$_2$—) 2.50-2.53 (2H, t, —CH$_2$—CH$_2$—NH—C(=O)—CH$_2$—CH$_2$-Maleimide) 2.77 (2H, m, CF$_3$C(=O)$_2$O$^-$.NH$_3^+$—CH$_2$—CH$_2$—) 3.21-3.24 (2H, m, CF$_3$C(=O)$_2$O$^-$.NH$_3^+$—CH$_2$—CH$_2$—) 3.40-3.80 (182H, m, —CH$_2$(O CH$_2$CH$_2$)$_m$OCH$_2$—CH$_2$—), (2H, t, —CH$_2$(OCH$_2$CH$_2$)$_m$O CH$_2$—CH$_2$—), (2H, t, —CH$_2$(OCH$_2$CH$_2$)$_m$OCH$_2$—CH$_2$—), (2H, t, —CH$_2$(OCH$_2$CH$_2$)$_m$OCH$_2$—CH$_2$—) 6.27 (1H, s, —CH$_2$—CH$_2$—NH—C(=O)—CH$_2$—CH$_2$-Maleimide) 6.70 (1H, s, —CH$_2$—CH$_2$—NH—C(=O)—CH$_2$—CH$_2$-Maleimide)

GPC Analysis; weight-average molecular weight (Mn): 2,120, weight-average molecular weight (Mw): 2,195, polydispersity (Mw/Mn): 1.546, peak top molecular weight (Mp): 2,164

[Chem. 16]

(F)

Figure 3:
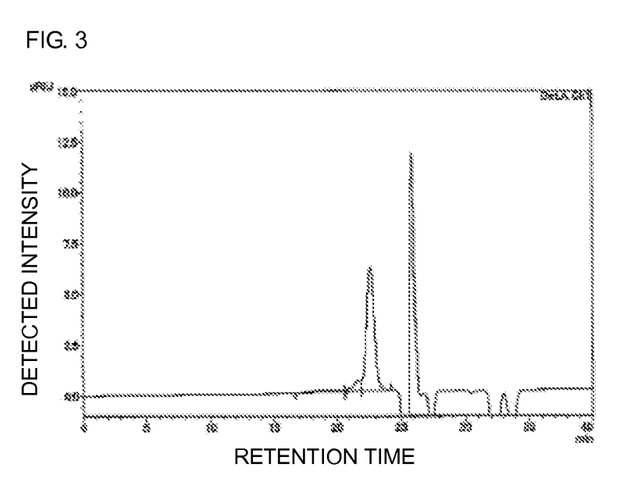
FIG. 3 shows GPC analysis results of a compound (F) obtained in Comparative Example 2.

Results obtained by analyzing the compound (F) by GPC were shown in FIG. 3. The content of each major component peak obtained from GPC analyses shown in FIGS. 2 and 3 was shown in Table 1. Furthermore, the compounds obtained in Example 1 and Comparative Example 2 were subjected to stability testing (at −20° C. for 1 week) and the results were summarized in Table 1.

TABLE 1

| GPC analysis | Before deprotection | After deprotection | After deprotection (−20° C., 1 week later) |
|---|---|---|---|
| Example 1 | 96% | 96% | 96% |
| Comparative Example 2 | 96% | 87% | 83% |

In Comparative Example 2, in which trifluoroacetic acid was used, polymeric substances were co-produced and the major component peak was reduced from 96% to 87% by 9% and was further reduced by 4% after storage at −20° C. for 1 week. In Example 1, in which methanesulfonic acid was used, the co-production of any polymeric substances was not observed and a state prior to deprotection was capable of being maintained after storage at −20° C. for 1 week.

[Industrial Applicability]

According to the present invention, the following lipid and method can be provided: a thiol-reactive polyoxyalkylene-modified lipid which has a small monoacyl lipid content and which can be one of functional materials useful in the field of drug delivery systems because biotoxicity and the self-degradation of liposomes due to contamination with a monoacyl lipid can be suppressed in the case of using the thiol-reactive polyoxyalkylene-modified lipid for raw materials for liposome formulations and a method for producing the same.

The invention claimed is:

1. A method for producing a polyoxyalkylene-modified lipid represented by the following formula (1), comprising Step (II) after Step (I):

wherein, R$^1$ and R$^2$ are hydrocarbon groups which are the same as or different from each other and which contain 4 to 24 carbon atoms, R$^3$ is a divalent hydrocarbon group containing 1 to 6 carbon atoms, OA is oxyalkylene groups containing 2 to 4 carbon atoms, n is the average addition mole number of the oxyalkylene groups and is 5 to 1,000, and Z is a group containing either maleimide or iodoacetamide;

Step (I): a step of obtaining a compound represented by the following formula (3) by deprotecting P of a compound represented by the following formula (2) with a methanesulfonic acid:

wherein, OA is oxyalkylene groups containing 2 to 4 carbon atoms, n is the average addition mole number of the oxyalkylene groups and is 5 to 1,000, R$^3$ is a divalent hydrocarbon group containing 1 to 6 carbon atoms, Z is a group containing either maleimide or iodoacetamide, and P is a chemically protected amino group which is to be deprotected with acid;

wherein, OA is oxyalkylene groups containing 2 to 4 carbon atoms, n is the average addition mole number of the oxyalkylene groups and is 5 to 1,000, R$^3$ is a divalent hydrocarbon group containing 1 to 6 carbon atoms, Z is a group containing either maleimide or iodoacetamide, and X is an ion pair of an amino group and the methanesulfonic acid;

Step (II): a step of obtaining the compound represented by Formula (1) in such a manner that a solution containing the compound represented by Formula (3) is added dropwise to a solution containing a compound represented by the following formula (4) to cause reaction:

(4)

wherein, $R^1$ and $R^2$ are hydrocarbon groups which are the same as or different from each other and which contain 4 to 24 carbon atoms and Y is an activated carbonate group.

2. The polyoxyalkylene-modified lipid-producing method according to claim 1, wherein Z is a group containing maleimide.

3. The polyoxyalkylene-modified lipid-producing method according to claim 1, wherein the chemically protected amino group P which is to be deprotected with acid is a t-butyl carbamate group.

* * * * *